United States Patent [19]
Pitre

[11] Patent Number: 4,793,805
[45] Date of Patent: Dec. 27, 1988

[54] APPARATUS AND METHOD FOR FORMING SHADE SAMPLES

[76] Inventor: Evard M. Pitre, 2611 Tangley, Houston, Tex. 77005

[21] Appl. No.: 900,373

[22] Filed: Aug. 26, 1986

Related U.S. Application Data

[63] Continuation-in-part of Ser. No. 766,895, Aug. 16, 1985, abandoned.

[51] Int. Cl.$^4$ .............................................. A61C 19/10
[52] U.S. Cl. ........................................ 433/26; 264/19
[58] Field of Search ............... 433/26, 213, 40, 34, 433/49, 229; 264/19, 20, 16

[56] References Cited

U.S. PATENT DOCUMENTS

| | | | |
|---|---|---|---|
| 868,109 | 10/1907 | Morris | 264/19 |
| 1,327,306 | 1/1920 | Berger | 433/26 |
| 2,434,416 | 1/1948 | Kohn et al. | 264/20 |
| 2,756,504 | 7/1956 | Levine | 433/26 |
| 3,702,027 | 11/1972 | Marshall et al. | 433/49 |
| 4,024,211 | 5/1977 | Strauss | 264/16 |
| 4,382,784 | 5/1983 | Freller | 433/26 |
| 4,474,499 | 10/1984 | Pedrazzini | 433/213 |
| 4,571,186 | 2/1986 | Pipko | 433/213 |

FOREIGN PATENT DOCUMENTS

| | | | |
|---|---|---|---|
| 1491108 | 7/1969 | Fed. Rep. of Germany | 433/26 |
| 2641740 | 3/1978 | Fed. Rep. of Germany | 433/26 |

Primary Examiner—John J. Wilson
Attorney, Agent, or Firm—Browning, Bushman, Zamecki & Anderson

[57] ABSTRACT

Disclosed are method and apparatus for forming tab samples of material, such as ceramic, having a metal or ceramic base. A form body comprises a recess between two extending arms and a shelf positioned to face the recess between the arms. A base may be positioned on and anchored to the shelf facing into the recess. Ceramic material may be formed on the base within the lateral confines of the recess as defined by the arms. Opaque ceramic material may be formed on the base as an underlayer of the ceramic sample. The ceramic may be fired on the base, and the finished ceramic sample may serve as a shade sample. Plastic or wax material may be formed on the shelf in a replica of such a base to construct a mold for use in forming the base.

6 Claims, 2 Drawing Sheets

U.S. Patent  Dec. 27, 1988  Sheet 1 of 2  4,793,805
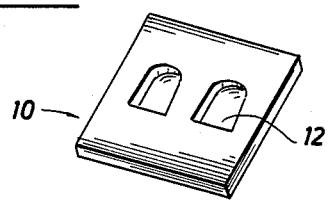
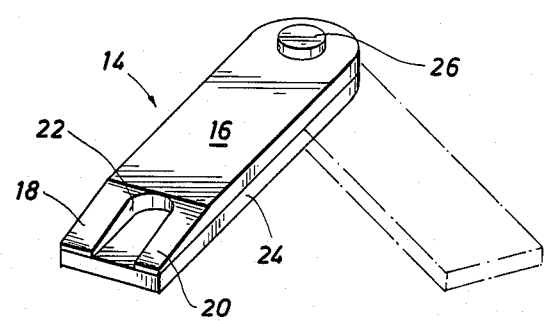
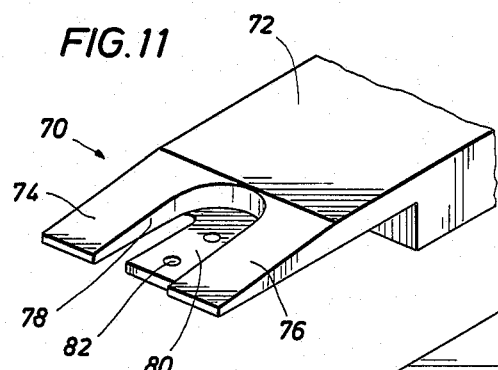
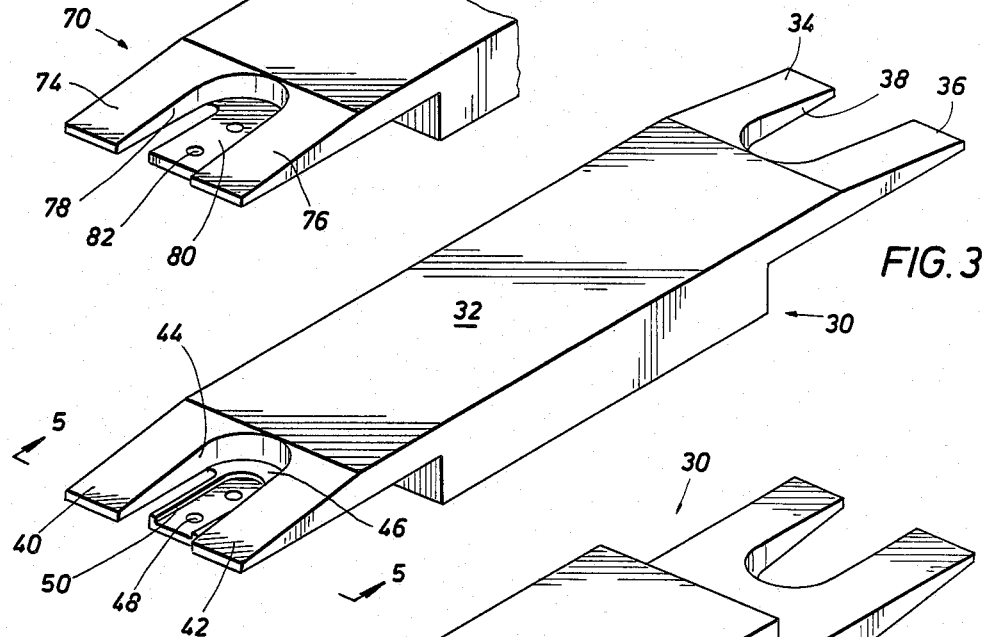
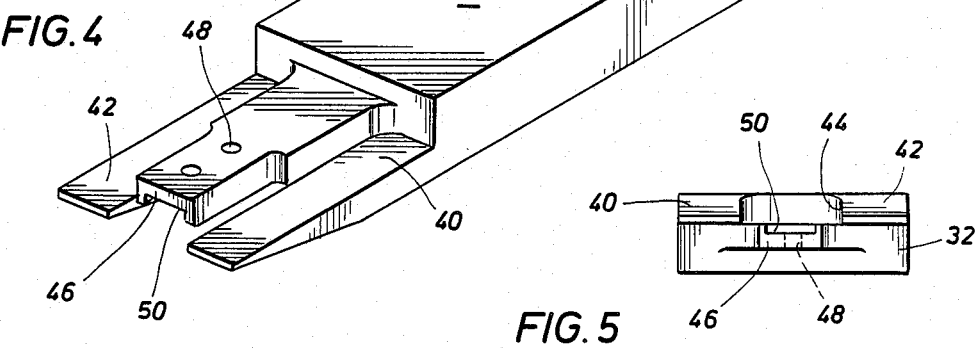
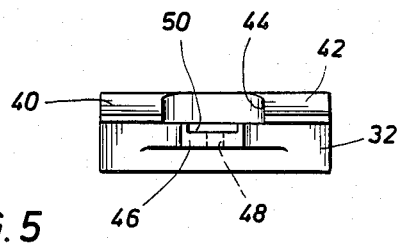

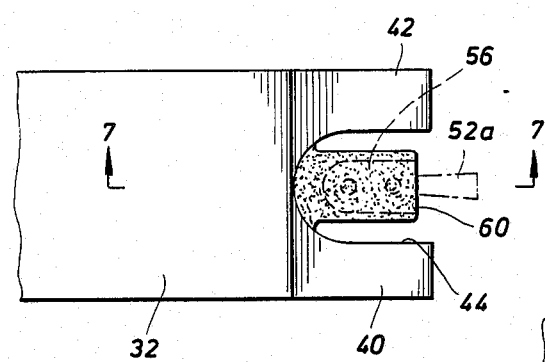
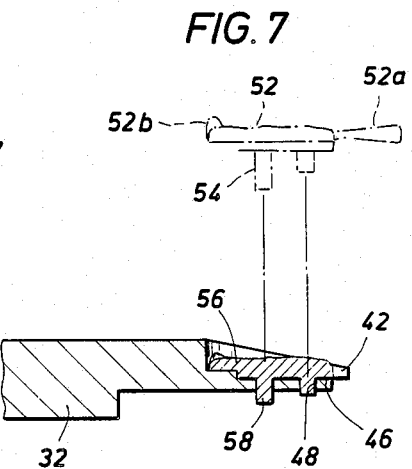
FIG. 6
FIG. 7
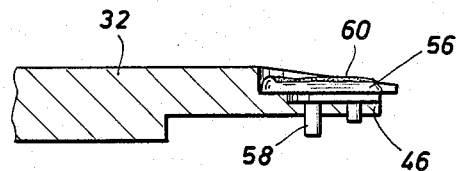
FIG. 8
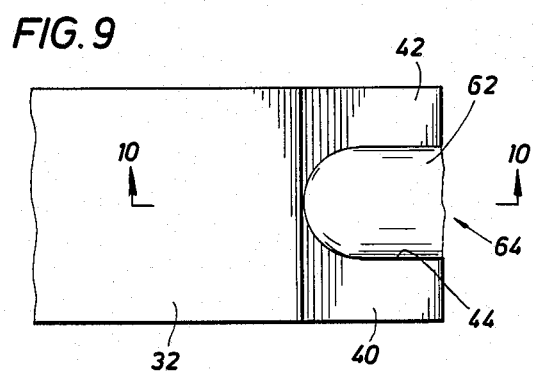
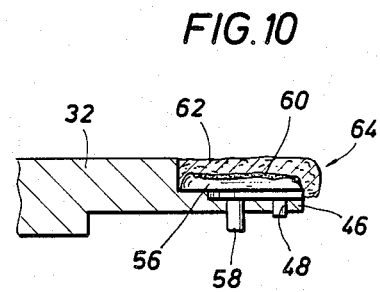
FIG. 9
FIG. 10
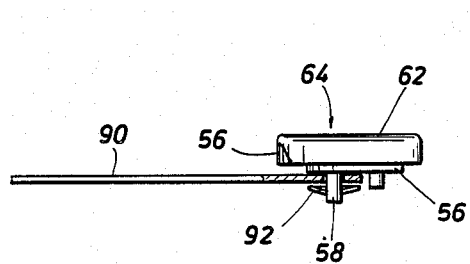
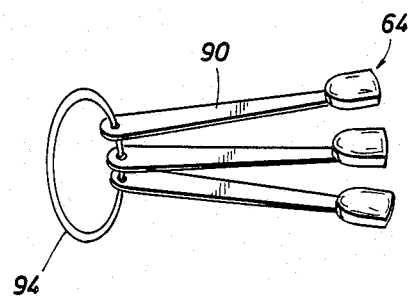
FIG. 12
FIG. 13

APPARATUS AND METHOD FOR FORMING SHADE SAMPLES

CROSS REFERENCE TO RELATED APPLICATION

This is a continuation-in-part application of co-pending U.S. patent application Ser. No. 766,895 filed Aug. 16, 1985 now abandoned.

BACKGROUND OF THE INVENTION

1. Field of the Invention

The present invention pertains to methods and apparatus for making shade guides. More particularly, the present invention relates to techniques for constructing samples of ceramic materials, such as porcelain, and particularly provides a technique for constructing such samples on a metal or ceramic base, for example. The porcelain samples so produced are readily usable as shade samples whereby the shade of a porcelain formation may be anticipated so that appropriate porcelain powders may be slected to achieve the desired shade.

2. Description of the Prior Art

Dental prostheses, including crowns and "false teeth" mounted on a bridge or plate, are generally made, at least in part, utilizing porcelain as a close approximation of the finish of natural teeth. For both terapeutic and cosmetic purposes, the prosthesis is generally shaped to approximate the shape of the tooth, or portion thereof, which the prosthesis is replacing. It is also important for cosmetic purposes that the coloring of the prosthesis match the remaining portion of the natural tooth to which the prosthesis is being added, or, in the case of a complete cap or complete prosthesis, that the color match the remaining teeth and/or prostheses in the mouth.

Typically, porcelain prostheses are made by dental technicians utilizing one or more powders mixed with water or other liquid to form the porcelain. The dentist must convey to the technician appropriate information to enable the technician to reproduce the desired prosthetic coloring. The technician may even have access to the patient to carry out the color matching. The selecting of coloring is done by selection of the powder or powders obtained from the manufacturer of same, the different porcelain powders providing different coloring when mixed with liquid, formed and fired in a kiln in the usual fashion of constructing porcelain finishes. Thus, the technician must know in advance which powder or powders to use to obtain a porcelain prosthesis finished with the desired coloring.

Various manufacturers currently provide samples of the porcelain finishes in the form of tabs made from the different powders supplied by the respective manufacturers. The intention is that the technician, or dentist, may compare the various tabs, referred to as shade tabs, to the desired coloring and then, based on the comparison, select the powder or powders to use to construct the prosthesis. However, it may be expected that each manufacturer's powders are unique, and further that powders of the same kind from a given manufacturer, although intended to be consistent, may vary from batch to batch. The result is that a dental technician may be required to acquire a shade tab for each powder from each batch of porcelain powders obtained from a given manufacturer. Additionally, where the technician must mix two or mor powders to achieve a porcelain finished with a particular coloring, the technician would most certainly have to obtain a shade tab utilizing such a mixture to anticipate its coloring.

A currently available form for molding a porcelain sample is shown generally at 10 in FIG. 1. The form 10 is essentially a slab of elastic material with one or more (two are shown) shaped recesses 12 into which a mixture of ceramic powder and liquid may be positioned to form a stylized tooth shape of the type generally used as shade tab samples. The flexibility of the form allows the hardened porcelain to be readily removed for firing.

Another forming device currently available is shown generally at 14 in FIG. 2, and includes a metal body 16 with two arms 18 and 20 extending from one end thereof to define a recess 22 between the arms. Moistened ceramic powder is pressed into the recess 22 which again takes the general stylized tooth shape. A planar member 24, also of metal, is connected to the body 16 by an axle 26 so that the member 24 may be selectively moved under the recess 22 as illustrated, or turned aside as shown in phantom to open the recess from the bottom. The member 24 is used as a convenience in forming the porcelain mixture within the recess 22, but may be replaced by tissue paper or the like held under the recess as the procelain is molded in place. The top surfaces of the arms 18 and 20 are sloped to facilitate forming a tapered stylized tooth shape, if desired, by permitting a flat surface to be moved over or pressed against the ceramic material in the recess 22.

Each of the molding tools illustrated in FIGS. 1 and 2 may be used to produce a porcelain-only shade tab of the type generally provided by porcelain powder manufacturers. However, the shade of a prosthesis is somewhat complex, referring to the hue, or color, of the finished product, its chroma, or intensity of hue, and the amount of grayness as opposed to whiteness that appears in the finish porcelain, which quantity is referred to as the value of the shade. Determination and anticipation of these shade qualities in the case of a porcelain sample for use in constructing a dental prosthesis are complicated by the fact that such prostheses are not entirely constructed from porcelain, with the exception of some cases including porcelain jacket crowns, and "false teeth" constructed to be mounted on a plate or the like. In general, a cap, or crown, is built up by first forming a metal or ceramic base which is shaped to fit over the remnant of the tooth root that remains after preparation of the tooth for capping. The base is covered with an intermediate layer of opaque ceramic material to mask the metal or ceramic substructure, and the finish porcelain, which is exposed and visible, is built up on the intermediate layer. The entire cap can then be fired and glazed in a kiln, and mounted on the root remnant by cementing the base to the remnant.

While only the finish porcelain surface is directly visible with the prosthesis properly mounted in the mouth of the patient, nevertheless, the opaque layer contributes to the shading of the finished prosthesis including one or more of the features of hue, chroma and value. For example, a finish porcelain layer, which may be somewhat translucent, may look darker, that is, exhibit more grayness, on an opaque layer over a ceramic base than a like finish layer on the same base without an opaque underlayer. In the more common case of a metal base, the finish layer directly on the base would appear darker than a finish layer over an opaque intermediate ceramic layer. Shade tabs currently acquired by dental technicians or constructed by them are generally made solely of the porcelain which will be used only in the finish layer of the prosthesis. Consequently, the effect of an opaque intermediate layer does not contribute to the shading of the ceramic shade samples currently being used.

It is desirable and would be highly advantageous for dental technicians to have available shade tabs constructed generally as caps or crowns are constructed, that is, with a finish porcelain layer overlying an intermediate opaque ceramic layer which in turn is mounted on a metal or ceramic backing. Further, it would be desirable and advantageous for the dental technician to have the capability of readily and rapidly making such structured shade tabs utilizing the various porcelain powders currently available from manufacturers as needed. Such capabilities for manufacturing shade tabs that more accurately reflect the shading of finished prosthesis would further aid the technician in customizing shading of prosthesis by mixing two or more such manufacturers' powders to achieve the desired coloring, since a source of error inherently a part of current shade tab technology, that is, the lack of consideration for the contribution of the opaque ceramic layer of the prosthesis, could be avoided.

SUMMARY OF THE INVENTION

The present invention provides method and apparatus for forming tab samples of ceramic materials, such as porcelain or the like, whereby the shade or coloring of the samples may be readily discerned and utilized. A former body includes a pair of arms extending in opposed relationship to define a recess therebetween, and a shelf positioned to face into the recess to support a backing, or base, the shelf also including the capability for anchoring the base thereto against relative motion. When the backing is so positioned on and anchored to the shelf, ceramic material may be formed on the backing within the lateral confines of the recess defined by the arms. The anchoring mechanism of the shelf may include one or more holes for receiving posts carried on one side of the backing.

Material such as plastic or wax, or the like, may be formed on the shelf in a replica of the backing. The shelf may feature an indentation facing into the recess to receive the material and facilitate its forming. The replica so formed may be utilized to construct a mold to cast a metal base or to pack a ceramic base. Such a plastic, or wax, replica may be pre-formed in the shape of the desired base, that is, of a body with one or more anchoring posts extending from one side for anchoring to the shelf of the forming body.

In a method of the invention, a tab or sample of ceramic material, such as porcelain, is constructed by providing a form body with two extending arms forming a recess therebetween and a shelf positioned to face into the recess, placing a base on the shelf and anchoring the base against movement relative thereto, and forming ceramic material on the base within the lateral confines of the recess defined by the arms. The tab or sample, including the base, may be completed by firing in a kiln. Further, the construction of ceramic on the base may include forming an opaque underlayer of ceramic on the base, and then forming the finishing ceramic on top of the intermediate layer. The base may be so anchored to the shelf by one or more posts of the base received in appropriate holes in the shelf.

A method of the invention may further include the steps of forming a replica of a base on the shelf using material such as plastic, or wax, or the like, and making a mold from the replica to cast or pack the base. Thereafter, the base may be mounted on the shelf as described above in the formation of the ceramic tab. To facilitate forming the replica, the shelf may feature an indentation facing the recess to receive and hold such replica material.

While the recess is illustrated herein as between two arms on a former body, the recess may be provided in any form on the former body. By a shelf is meant any surface facing into the recess for receiving a base, or replica thereof, for example, and could be provided by the bottom of the recess.

The present invention thus provides a technique for constructing shade tabs which include a finish ceramic layer over an opaque intermediate ceramic layer covering a backing or base, generally mimicking the layered construction of dental prosthesis for the benefit of a dental technician or dentist using such a shade tab to compare shading of an anticipated finished prosthesis with desired shading.

BRIEF DESCRIPTION OF THE DRAWINGS

FIG. 1 is a perspective view of an available elastic form for use in making all-porcelain samples as discussed hereinbefore;

FIG. 2 is a perspective view of another available device for use in constructing all-porcelain samples as discussed hereinbefore, with the device of FIG. 2 shown in two configurations;

FIG. 3 is a perspective view of a shade tab former according to the present invention, and including, at one end thereof, partial construction of the currently available device illustrated in FIG. 2;

FIG. 4 is a perspective view of the shade tab former according to the present invention as shown in FIG. 3, but illustrated inverted from the orientation of FIG. 3;

FIG. 5 is an end view of the shade tab former as illustrated in FIG. 3;

FIG. 6 is a fragmentary plan view of the shade tab former of FIGS. 3–5, illustrating the positioning of a backing with an opaque intermediate ceramic layer positioned thereon;

FIG. 7 is a side elevation in cross section of the fragment of the form body taken along line 7—7 of FIG. 6 and, in exploded view, indicating the utilization of a base replica for preparation of a base or backing;

FIG. 8 is a view similar to FIG. 7 but showing the addition of the opaque ceramic underlayer on the base;

FIG. 9 is a view similar to FIG. 6 but showing the addition of a finish porcelain layer to the ceramic sample;

FIG. 10 is a view similar to FIGS. 7 and 8, but taken along line 10—10 of FIG. 9 to show, in cross section, the multiple layers of ceramic built up on the base;

FIG. 11 is a fragmentary, perspective view of another preferred version of a form body for use in constructing shade tabs according to the present invention;

FIG. 12 is a fragmentary side elevation in partial section of a shade tab formed according to the present invention and mounted on an elongate holder; and FIG. 13 is a pictorial representation of three such holders positioned on a ring and on which are mounted shade tabs according to the present invention.

DESCRIPTION OF PREFERRED EMBODIMENTS

A shade tab forming body is shown generally at 30 in FIGS. 3 and 4, and includes a body proper 32. For convenience, two opposed arms 34 and 36, defining a recess 38 therebetween, extend from one end of the body 32 in the manner of the opposed arms 18 and 20 of the body 16 of the currently available device illustrated generally at 14 in FIG. 2. As noted hereinbefore, an all-ceramic shade tab may be formed within the recess between the arms 34 and 36 with the aid, if necessary, of a piece of tissue paper or the like held below the recess to aid in forming the ceramic within the recess. The arms 34 and 36 are tapered downwardly to allow the ceramic to be smoothed with a flat surface, if necessary, to form a tab with a thinner edge and a thicker edge. More particularly, however, the body 32 includes, at its opposite end, a pair of opposed arms 40 and 42 extending outwardly to form a recess 44 therebetween, both arms being sloped downwardly on their top surfaces generally after the fashion of the arms 34 and 36 to provide a tapering shade tab. Facing into the recess 44 at its bottom extent is a ledge, or shelf, 46 which generally has a narrower lateral dimension than the width of the recess 44 between the arms 40 and 42. One or more (two are shown) holes 48 extend into and through the shelf 46 to receive anchroing posts as discussed in detail hereinafter. The shelf 46 is constructed to include an optional indentation 50 facing into the recess 44 for a purpose discussed hereinafter. Details of the construction of the shelf 46 and of the arms 40 and 42 may be further appreciated by reference to FIG. 5.

In FIGS. 6 and 7, use of a plastic or wax form or the like 52 is indicated in phantom. The device 52 may be pre-formed and provided with a sprue 52a to facilitate handling. Aside from the sprue 52a, the form 52 is a replica of the shape desired for a metal or ceramic backing, or base, on which a ceramic tab is to be constructed. In particular, the replica 52 is generally elongate and flat, with one end (opposite the sprue 52a in FIG. 7) possibly wider than the other end, and featuring one or more (two are shown) posts 54 extending downwardly to be received within anchoring holes 48 of the shelf 46. As an optional feature, the plastic form 52 may include an upwardly-extending lip 52b for the purpose of forming a like lip on a base for use in backing the shade tab. Also, the top surface of the replica 52, and subsequent base, need not be flat, but may be convex or concave.

Such a base replica 52 may be formed directly on the shelf 46 within the lateral confines of the recess 44 as defined by the arms 40 and 42, with the replica material passing through the post holes 48 to form the anchoring posts 54. When wax is used to form the replica 52, the wax is heated to become molten, and is then built up and shaped on the ledge 46 where it is allowed to harden. The optional indentation 50 may be provided in the shelf 46 to receive material and assist in holding it in place on the shelf as the material is formed into the replica 52. The lateral extent of the replica as thus formed should be the same as that desired for a backing for a shade tab. The plan view of such a replica is indicated with the dashed lead line to 56 in FIG. 6, and side elevations are shown in FIGS. 7 (in cross section) and 8. With the plastic, or wax, replica 52 appropriately formed, the replica is removed from the former body 30 and a mold (not shown) may be constructed from the replica 52 utilizing a lost-wax type process, for example. Such a mold may then be utilized to cast a metal base, or backing, 56 having anchoring posts 58, or may be packed with ceramic material to form a like ceramic base 56. Alternatively, such a plastic or wax replica may be pre-formed for use in the casting or packing process. Further, such metal or ceramic bases 56 may be pre-formed and provided for direction use with the shade tab former 30.

To continue with the production of a shade tab according to the present invention, a metal or ceramic base 56 is mounted on the ledge 46 with the anchoring posts 58 extending through the post holes 48 to prevent movement of the base relative to the ledge. Thereafter, ceramic or other material may be built up on the base 56 as desired. In particular, an opaque intermediate ceramic layer 60 may be used to cover the top of the base 56 as indicated in FIGS. 6 and 8. The ceramic is obtained in the usual manner, that is, by mixing ceramic powder with water or other liquid to form a material which can be coated onto the base 56. The intermediate ceramic layer 60 is opaque to mimic an opaque ceramic layer used in making a prosthesis whose shade is to be determined. With the ceramic layer 60 in place, a finish ceramic layer 62 may be stacked onto the opaque intermediate layer and whatever surface of the base 56 is visible from the top and sides of the construction as desired to complete the building of the tab shown generally at 64 in FIGS. 9 and 10. While the intermediate layer 60 may be confined laterally to the extent of the backing 56 is desired, as shown in FIG. 6, the finish porcelain layer 62 may extend laterally beyond the limits of the base 56 and intermediate opaque ceramic layer to fill the lateral confines of the recess 44, for example, as shown in FIG. 9. Alternatively, the lateral extent of the finish ceramic layer 62 may be limited to something less than the dimensions of the recess 44 as desired. A knife or other hand tool may be utilized in shaping the ceramic layers 60 and 62, for example. A flat surface (not shown) may be used to slope the top of the tab 64 along the lines of the tops of the former arms 40 and 42 if desired.

When the ceramic layers 60 and 62 have been completely applied to the coping 56, the tab 64 may be removed from the former body 32 by pushing on the posts 58 with a hand tool, for example, or otherwise lifting the tab from the ledge 46. Further trimming may be done to the tab 64 as desired, and the tab may be fired in a kiln (not shown) and glazed as required.

Another preferred embodiment of the present invention is shown generally at 70 in FIG. 11, comprising a former body 72 with opposed arms 74 and 76 extending outwardly to define a recess 78 therebetween. A ledge 80, of generally narrower lateral dimension than the recess 78, extends to face upwardly into the recess. The ledge 80 includes anchoring post holes 82 after the fashion of the post holes 48 of the shade tab former shown generally at 30 in FIGS. 3 and 4. However, the shelf 80 may feature a smooth top surface as opposed to an indentation 50 of the shade tab former 30. Thus, the ledge 80 may be preferred for use with pre-formed bases 56, which may also be flat-bottomed except for anchoring posts 58. However, plastic or wax material base replicas may still be formed on the ledge without the assistance of an indentation, and used to obtain a mold of a base. In all respects other than the use of a shelf indentation, the shade tab former shown generally at 70 may be used to produce ceramic shade tabs in the same manner as the forming body 30, including use to support and anchor a base on which ceramic layers may then be formed to produce a shade tab as discussed hereinbefore. Again, the top surfaces of the body arms 74 and 76 are sloped so that, if desired, the shade tab may be readily smoothed to a tapered finish.

In FIG. 12, a shade tab 64 is shown mounted on an elongate holder 90 by means of one of the anchoring posts 58 passing through an appropriate hole in the holder and receiving a snapon washer 92 which prevents the post 58 from being withdrawn from the holder hole, but which permits rotation of the shade tab about the post within the hole relative to the holder. The anchor post 58 so used may be formed with a nub over which the washer 92 may be forced so that the nub prevents the washer from slipping off of the post. In FIG. 13, three such holder-mounted shade tabs 64 are shown mounted on a ring 94 which passes through an appropriate hole at the opposite end of each of the holders 90. Thus, the shade tabs 64 may be conveniently mounted for use and ready reference in the dental laboratory or dental office. Other techniques for mounting shade tabs 64 may also be utilized.

The present invention thus provides a technique for constructing a shade tab or porcelain in which the finish porcelain layer is backed by an opaque ceramic layer mounted on a metal or ceramic backing, or base, in much the same fashion that a crown or cap is constructed of multiple layers of ceramic, including an opaque underlayer for example, all being mounted on a metal or ceramic support or backing.

The foregoing disclosure and description of the invention is illustrative and explanatory thereof, and various changes in the method steps as well as the details of the illustrated apparatus may be made within the scope of the appended claims without departing from the spirit of the invention.

What is claimed is:

1. A method of forming a shade tab comprising the following steps:
   a. providing a former body including a recess between two opposed arms thereof, and having a shelf facing into said recess wherein said shelf has at least one hole;
   b. mounting a base on said shelf within the lateral confines of said recess, and anchoring said base to said shelf by at least one post positioned within a respective hole in said shelf;
   c. positioning opaque ceramic material on said base generally within the confines of said recess;
   d. positioning finish ceramic material on said opaque ceramic material;
   e. removing said base, with said opaque and finish ceramic material, from said recess; and
   f. firing said tab.

2. A method as defined in claim 1 further comprising the following additional steps:
   a. forming a replica of such a base on said shelf;
   b. constructing a mold from said replica; and
   c. forming said base with said mold.

3. A method as defined in claim 2 wherein said replica comprises wax.

4. A method as defined in claim 2 wherein said replica comprises plastic.

5. A method as defined in claim 1 wherein said base comprises metal.

6. A method as defined in claim 1 wherein said base comprises ceramic.

* * * * *